United States Patent [19]

Reimels

[11] Patent Number: 4,693,246
[45] Date of Patent: Sep. 15, 1987

[54] SUTURE TYING FORCEPS

[75] Inventor: Harry G. Reimels, Braintree, Mass.

[73] Assignee: Mentor D & O, Inc., Norwell, Mass.

[21] Appl. No.: 720,505

[22] Filed: Apr. 5, 1985

[51] Int. Cl.[4] .............................................. A61B 17/28
[52] U.S. Cl. .................................... 128/321; 128/354; 81/418; 81/424.5
[58] Field of Search ............... 128/354, 321, 322, 325; 81/418, 419, 424.5, 426, 426.5; 72/409; 140/106

[56] References Cited

U.S. PATENT DOCUMENTS

| | | | |
|---|---|---|---|
| 391,227 | 10/1888 | Buckman | 72/409 |
| 404,811 | 6/1889 | Wichelhaus | 81/426 |
| 511,091 | 12/1893 | Neuhaus | 81/426 |
| 1,619,084 | 3/1927 | Miller | 72/409 |
| 1,767,175 | 9/1929 | Glass | 128/354 |
| 2,618,268 | 11/1952 | English | 128/321 |
| 2,668,538 | 2/1954 | Baker | 128/346 |
| 2,726,657 | 12/1955 | Tabrah | 128/321 |
| 2,743,726 | 5/1956 | Grieshaber | 128/321 |
| 3,589,369 | 6/1971 | Alkshis | 128/321 |
| 3,608,554 | 9/1971 | McGuinness | 128/321 |
| 3,916,909 | 11/1975 | Kletschka | 128/321 |
| 3,921,640 | 11/1975 | Freeborn | 128/321 |
| 3,972,333 | 8/1976 | Leveen | 128/354 |
| 4,043,343 | 8/1977 | Williams | 128/321 |
| 4,446,866 | 5/1984 | Davison | 128/321 |
| 4,461,297 | 7/1984 | Sutter | 128/354 |

FOREIGN PATENT DOCUMENTS 214727 2/1924 Fed. Rep. of Germany ...... 128/354

*Primary Examiner*—Richard J. Apley
*Assistant Examiner*—H. Macey
*Attorney, Agent, or Firm*—Morse, Altman & Dacey

[57] ABSTRACT

Suture tying forceps of improved construction are disclosed which materially reduce a suture being flexed therein from breaking. The suture typing forceps include a pair of members mounted in the free ends of a pair of gripping arms integrally joined at one end. The members terminate in a pair of suture tying tips, respectively featuring a pair of complementary mating surfaces serving as suture clamping surfaces. For the most part, the suture clamping surfaces are designed to clamp a suture segment which is about ten times the thickness of the suture. The suture clamping surfaces further are designed to define a flexing angle transversely thereof which is less than a right angle.

5 Claims, 12 Drawing Figures

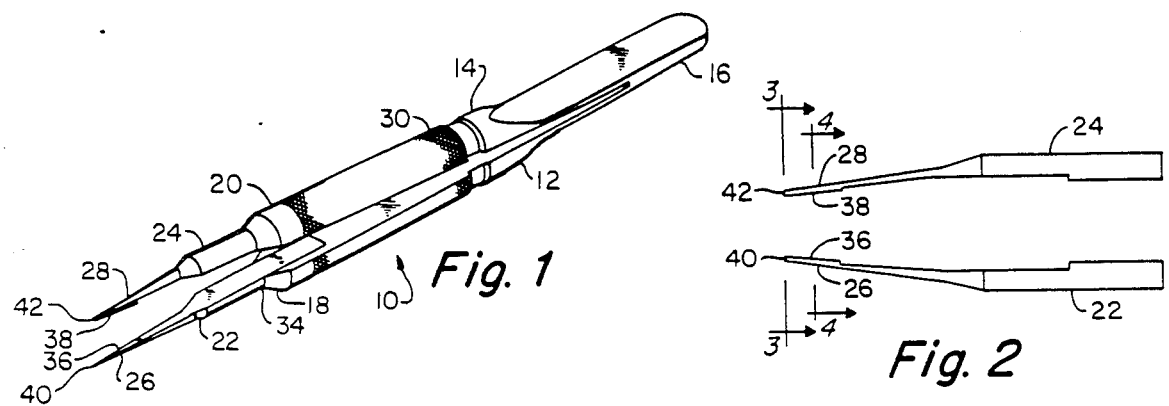
Fig. 1
Fig. 2
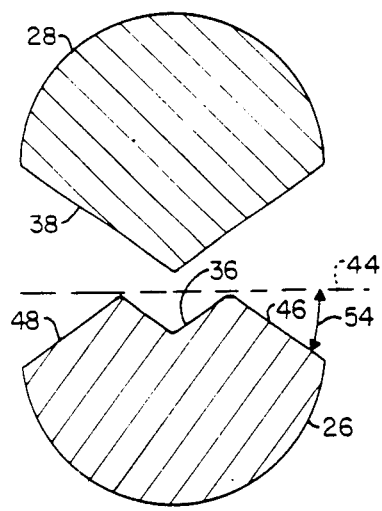
Fig. 3
Fig. 4
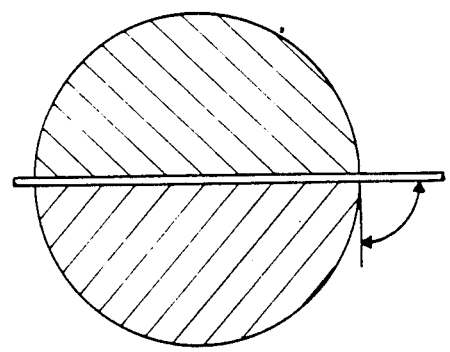
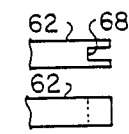
Fig. 5
Fig. 6
Fig. 7
Fig. 8
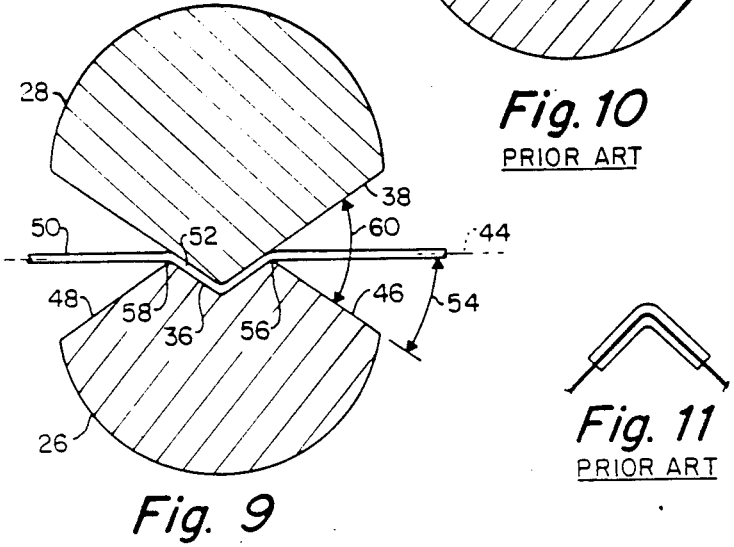
Fig. 9
Fig. 10
PRIOR ART
Fig. 11
PRIOR ART
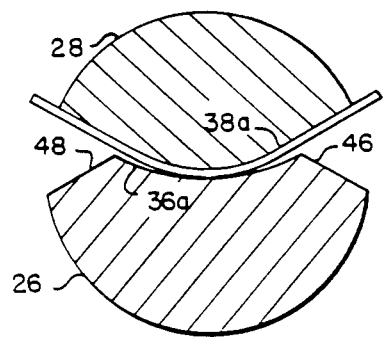
Fig. 12

SUTURE TYING FORCEPS

BACKGROUND OF THE INVENTION

1. Field of the Invention

The present invention relates generally to forceps and, more particularly, to suture tying forceps which reduce suture breakage.

2. The Prior Art

Suture tying forceps are used at the completion of surgery to close the incision. Such closing is effected, among others, by knots, threads or sutures manipulated by a surgeon with the aid of the forceps. The forceps must provide adequate control of the sutures or threads without breaking them. This is of particular concern in microsurgery, such as involving the eye, where the threads and sutures of necessity must be very thin indeed. A break of such a fine suture when closing after, say cataract surgery, at the least prolongs the operation and at the worst can endanger the results of the operation. Yet, present day suture tying forceps unduly expose the threads and the sutures to radical bends and high stress concentrations during their use.

SUMMARY OF THE INVENTION

It is a principal object of the present invention to overcome the above disadvantages by providing suture tying forceps of improved construction that materially reduces the risk of a thread or a suture being manipulated thereby from breaking.

More specifically, it is an object of the present invention to provide suture tying forceps which limit the flexing of delicate sutures during their use comprising a pair of members mounted in the free ends of a pair of gripping arms which are integrally joined at one end. The pair of members terminate in a pair of suture tying tips. A pair of complementary mating surfaces are formed respectively on the tips and are designed to clamp a segment of a suture therebetween in such a way as to limit the flexing thereof when twisting the suture thereby. Preferably, the length of the clamped segment is not more than about ten times the thickness of the suture. One of the pair of suture tying tips, in forming one of the pair of complementary mating surfaces, defines a V-shaped form in right cross section along its axial length, with the V-shaped form defining an obtuse angle. The other of the pair of suture tying tips, in forming the other one of the pair of complementary mating surfaces, has a cross sectional configuration near its free end which is different from a cross sectional configuration substantially along its axial length beyond its free end. At its free end, the cross sectional configuration includes a U-shaped form, and beyond its free end, the cross sectional configuration comprises both the U-shaped form, defining an obtuse angle, and acute-angled flexing surfaces formed adjacent to and contiguous with the U-shaped form. The flexing surfaces, together with the V-shaped form, define flexing angles which are less than right angles. It is the V-shaped and U-shaped forms that respectively comprise the pair of complementary mating surfaces which serve as the suture clamping surfaces. Preferably, the gripping arms are knurled at their outer peripheries. Preferably, the forceps are made of sterilizable material, including by autoclaving, such as stainless steel. Preferably, the complementary mating surfaces unite progressively away from the free ends of the pair of suture tying tips when the gripping arms are compressed. Preferably, the suture tying forceps are provided with means precisely to align the pair of suture tying tips so that the complementary mating surfaces mate and remain mated when manipulating a suture clamped therebetween.

Other objects of the present invention will in part be obvious and will in part appear hereinafter.

The invention accordingly comprises the suture tying forceps of the present disclosure, its components, parts and their interrelationships, the scope of which will be indicated in the appended claims.

BRIEF DESCRIPTION OF THE DRAWINGS

For a fuller understanding of the nature and objects of the present invention, reference is to be made to the following detailed description, which is to be taken in connection with the accompanying drawings, wherein:

FIG. 1 is a perspective view of suture tying forceps constructed in accordance with the present invention;

FIG. 2 is in elevation and on an enlarged scale depicting parts of the suture tying forceps of FIG. 1;

FIG. 3 is a cross section, on an enlarged scale, of the parts of FIG. 2 along the line 3—3 thereof;

FIG. 4 is a cross section, on an enlarged scale, of the parts of FIG. 2 along the line 4—4 thereof;

FIG. 5 is a fragmentary plan view of a modified part shown in FIG. 2;

FIG. 6 is an elevation of the part of FIG. 5;

FIG. 7 is a fragmentary plan view of a second modified part shown in FIG. 2;

FIG. 8 is a elevation of the part of FIG. 7;

FIG. 9 is a view similar to the one shown in FIG. 4 but with a suture shown clamped in place;

FIGS. 10 and 11 depict, in cross section, prior art forceps; and

FIG. 12 is a view similar to FIG. 9 but illustrates a modified structure thereof.

DETAILED DESCRIPTION OF THE PREFERRED EMBODIMENT

In general, the illustrated embodiment of suture tying forceps 10 that materially reduces the likelihood of a suture 50 being flexed thereby from breaking comprises a pair of gripping arms 12 and 14 integrally joined at one end 16, with its free ends 18 and 20 normally being in radially spaced relation, and a pair of members 22 and 24 secured in and to the free ends 18 and 20, specifically within appropriate receptacles 34 respectively formed in the ends 18 and 20. The members 22 and 24 can be secured within the receptacles 34 in various known ways as, for example, by being welded therein. The members 22 and 24 terminate in a pair of suture tying tips 26 and 28 that taper toward their respective ends 40 and 42. On their mutually opposed faces, the suture tying tips 26 and 28 are provided with a pair of complementary mating surfaces 36 and 38, each defining an obtuse angle. These complementary mating surfaces 36 and 38 are designed to serve as clamping surfaces, securely to clamp a segment 52 of the suture 50 therebetween, observe FIG. 9. Preferably, the length of the clamped segment 52 is no greater than about ten times the thickness of the delicate suture 50. The complementary mating surfaces 36 and 38 are designed to limit the flexing of the suture 50 to less than a right angle, as will be more evident from below.

The complementary mating surfaces 36 and 38 can be formed smoothly or, if desired, with a finely roughened surface. Preferably, such finely roughened surface of the complementary mating surfaces 36 and 38 is conveniently effected during its formation by electrical discharge machining (EDM). As known, EDM forms the surfaces 36 and 38 by spark erosion, a precisely controllable manufacturing process, which results in such a finely roughened surface.

Preferably, the outer peripheries of the gripping arms 12 and 14 are provided with knurled surfaces 30, 30 to provide the surgeon with a secure grip thereon, even when operating in a wet field.

It will be understood that the ends 40 and 42 of the pair of suture tying tips 26 and 28 preferably are formed rounded, that is blunt, so as to minimize unintended injury to delicate membranes of the eye or other like parts, when in operative use. Immediately adjacent the rounded, blunt ends 40 and 42, the cross sectional configuration of the pair of suture tying tips 26 and 28 is as shown in FIG. 3. As will be noted therefrom, one 28 of the pair of suture tying tips 26 and 28 is formed with a V-shaped form, whose complementary mating surface 38 defines an obtuse angle, that is somewhat greater than a right angle. It has been found that such an obtuse angle provides the best combination of an assured clamping surface with adequate manipulative control that nevertheless poses little or no threat of damage even to the delicate suture 50 used in eye surgery. The second 26 of the pair of suture tying tips 26 and 28, also is formed with a V-shaped form, whose complementary mating surface 36 also defines an obtuse angle which is identical with the angle of the surface 38.

The cross sectional configurations of the pair of suture tying tips 26 and 28, as they prevail for the substantial portions of their respective axial lengths, are shown in FIG. 4. As will be noted, the cross section of the one 28 of the pair of suture tying tips 26 and 28 is similar to that immediately adjacent its blunt end 42, only its dimensions are greater due to the taper of the pair of members 22 and 24, in particular of the pair of suture tying tips 26 and 28 thereof toward their respective blunt ends 40 and 42. The cross section of the other one 26 of the pair of suture tying tips 26 and 28, on the other hand, here is different from that shown in and described with reference to FIG. 3, i.e., from the one immediately adjacent its blunt end 40.

As will be noted in FIG. 4, the V-shaped complementary mating surface 36 has remained essentially the same as regards both the angle and the lengths of its side surfaces forming the obtuse angle thereof. Unlike in FIG. 3 however, a pair of flexing surfaces 46 and 48 now are formed adjacent the V-shaped complementary mating surface 36. Each of these flexing surfaces 46 and 48 defines an acute angle 54, as measured from a line 44 tangential to the apices 56 and 58, and taken up by the respective ends of the suture 50 in FIG. 9. These acute-angled flexing surfaces 46 and 48 formed adjacent to and contiguous with the clamping surface 36 are designed to limit the downward flexing of the delicate suture 50 from the tangential line 44. Consequently, not only is the arcuate bending of the suture 50 at the apices 56 and 58 reduced but the suture 50 also is not subjected to high stress concentrations thereat when the suture 50 is flexed, i.e., twisted by the suture tying forceps 10 during their operative use. The upward flexing of the suture 50 is, on the other hand, limited by the V-shaped complementary mating surface 38. It is to be noted with the aid of FIG. 9 that the combined upward and downward flexing of the suture 50 beyond the apices 56 and 58, as represented by an angle 60, is still smaller than a right angle. Preferably, the apices 56 and 58 are slightly rounded, as shown in FIG. 9.

A modified structure of the pair of suture tying tips 26 and 28 is illustrated in FIG. 12. In this modified structure, the pair of suture tying tips 26 and 28 are formed with clamping surfaces 36a and 38a which are U-shaped, substantially as shown. Adjacent and contiguous with the U-shaped clamping surface 36a are flexing surfaces 46 and 48, which are substantially flat planar surfaces. Likewise, the opposed U-shaped clamping surface 38a also is formed, in a region opposite to the flexing surfaces 46 and 48, with substantially flat planar surfaces, contiguous with the U-shaped clamping surface 38a in its central region.

In contrast, conventional forceps, as illustrated in FIGS. 10 and 11, expose the sutures to radical bends of right angles in both directions and also to high stress concentrations at those bends.

In FIGS. 5-8 are fragmentarily depicted a modified pair of members 62 and 64, which in all respects are identical with the pair of members 22 and 24, except that the members 62 and 64 also are provided with means precisely and consistently to align their respective suture tying tips 26 and 28 so that their complementary mating surfaces 36 and 38 mate exactly and remain so mated when twisting a suture therebetween. This aligning means comprises a projecting stud 66 formed on member 64 and designed snugly to fit within an appropriately shaped receptacle 68 formed in the other member 62.

Preferably, the suture tying forceps 10 of the invention are formed of sterilizable material, such as stainless steel, which also is autoclavable.

Thus it has been shown and described suture tying forceps 10 of improved construction, which forceps 10 satisfy the objects and advantages set forth above.

Since certain changes may be made in the present disclosure without departing from the scope of the present invention, it is intended that all matter described in the foregoing specification or shown in the accompanying drawings, be interpreted in an illustrative and not in a limiting sense.

What is claimed is:

1. Suture tying forceps comprising:
   (a) a pair of gripping arms integrally joined at one end, with the free ends thereof being normally in radially spaced relation;
   (b) a pair of members respectively secured in said free ends of said pair of gripping arms and terminating in a pair of suture tying tips;
   (c) said pair of suture tying tips formed with respective complementary mating surfaces designed to clamp a suture therebetween;
   (d) one of said pair of suture tying tips having a longitudinal U-shaped groove providing a cross sectional configuration comprising a U-shaped clamping surface and a pair of substantially flat planar flexing surfaces being contiguous with and extending downwardly from said U-shaped clamping surface;
   (e) the other of said pair of suture tying tips having a cross sectional configuration comprising a longitudinal U-shaped form in its central region and a second pair of substantially flat planar flexing surfaces being contiguous with and extending upwardly from said U-shaped form.

2. The suture tying forceps of claim 1 wherein said one of said complementary mating surfaces in cooperation with said pair of substantially flat planar flexing surfaces define a flexing angle which is less than 90°.

3. The suture tying forceps of claim 1 wherein said pair of members are provided with means to align said pair of suture tying tips so that said complementary mating surfaces mate and remain mated when said forceps is operatively twisting said suture.

4. Suture tying forceps comprising:
(a) a pair of gripping arms integrally joined at one end, with the free ends thereof being normally in radially spaced relation;
(b) a pair of members respectively secured in said free ends of said pair of gripping arms and terminating in a pair of suture tying tips;
(c) said pair of suture tying tips formed with respective complementary mating surfaces designed to clamp a suture therebetween;
(d) one of said pair of suture tying tips having a longitudinal V-shaped groove providing a cross sectional configuration comprising a V-shaped clamping surface and a pair of substantially flat planar flexing surfaces being contiguous with and extending downwardly from said V-shaped clamping surface;
(e) the other of said pair of suture tying tips having a cross sectional configuration comprising a longitudinal V-shaped form in its central region and a second pair of substantially flat planar flexing surfaces being contiguous with and extending upwardly from said V-shaped form.

5. The suture tying forceps of claim 4 wherein one of said pair of complementary mating surfaces formed respectively on said pair of suture tying tips and said flexing surfaces adjacent said V-shaped clamping surface define a flexing angle transversely thereof which is less than a right angle.

* * * * *